United States Patent [19]

Holm

[11] Patent Number: 4,707,992

[45] Date of Patent: Nov. 24, 1987

[54] MICROWAVE RADIATING ANTENNAE HYDRAULIC ADJUSTMENT APPARATUS AND METHOD

[76] Inventor: Timothy R. Holm, 1739 E. Montebello, Phoenix, Ariz. 85016

[21] Appl. No.: 785,864

[22] Filed: Oct. 9, 1985

[51] Int. Cl.[4] ............................................. F15B 11/18
[52] U.S. Cl. .................................. 60/721; 91/167 R; 91/527; 91/530
[58] Field of Search ............... 60/571; 91/167 R, 527, 91/530; 92/2; 128/804

[56] References Cited

U.S. PATENT DOCUMENTS

| | | | |
|---|---|---|---|
| 2,714,906 | 8/1955 | Peterson | 91/167 R |
| 2,969,042 | 1/1961 | Litz et al. | 91/167 R |
| 3,306,539 | 2/1967 | Grimland | 91/167 R |
| 3,477,229 | 11/1969 | Katko | 91/167 R |
| 4,434,341 | 2/1984 | Busby | 128/804 X |

Primary Examiner—Edward K. Look
Attorney, Agent, or Firm—Harry M. Weiss & Associates

[57] ABSTRACT

A hydraulic adjustment apparatus for use in adjusting and positioning microwave radiating antenna or any other treatment monitoring device is disclosed. The hydraulic adjustment apparatus, generally comprises an upper portion having a box-like member suitable for accommodating therein a mounting member; a plurality of upper adjustable leg member means; a plurality of upper switch valve means with associated plurality of upper tubular means attached thereto; as well as a plate member for joining said upper portion to a lower portion of said hydraulic adjustment apparatus. Said lower portion, generally comprises a plurality of lower tubular members; and lower adjustable leg member means operably coupled to a base member having a preferable microwave radiating antenna or any other treatment monitoring device integrally coupled thereto.

9 Claims, 10 Drawing Figures

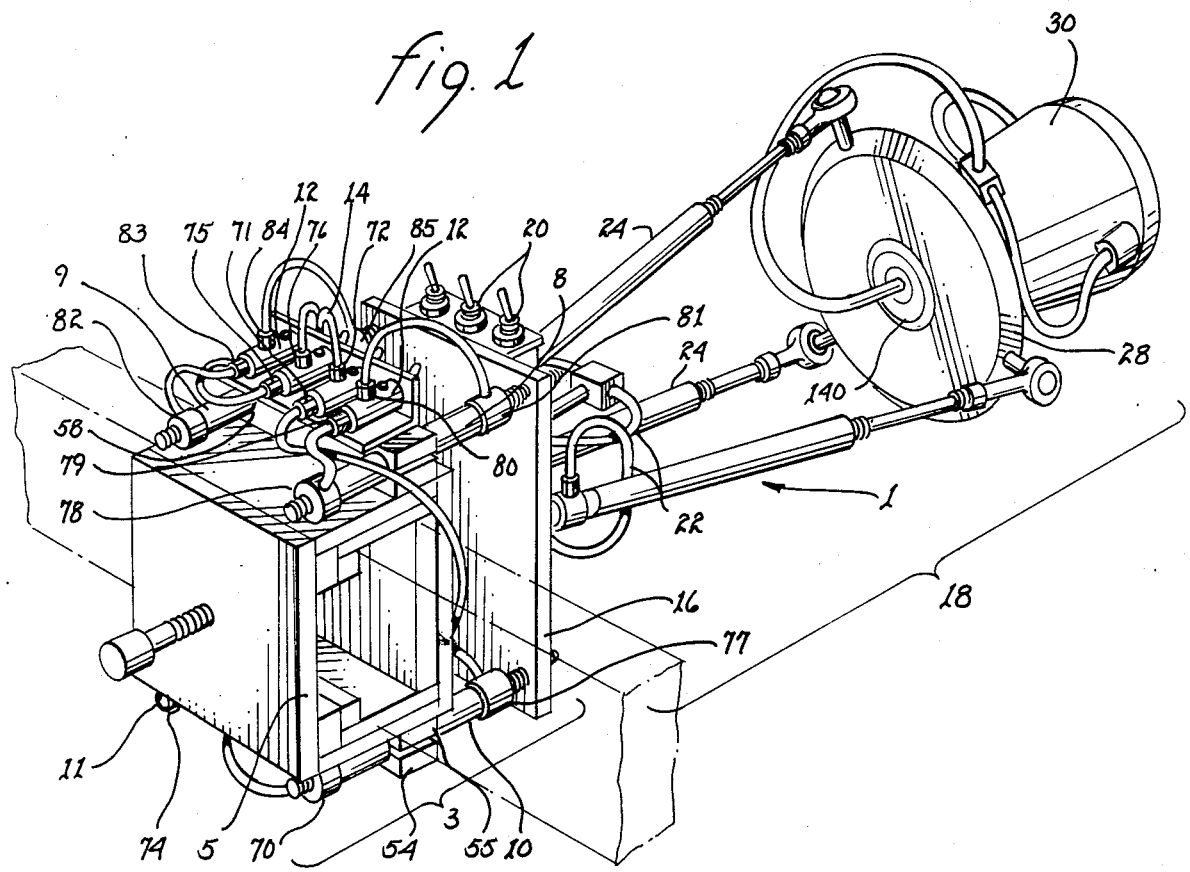
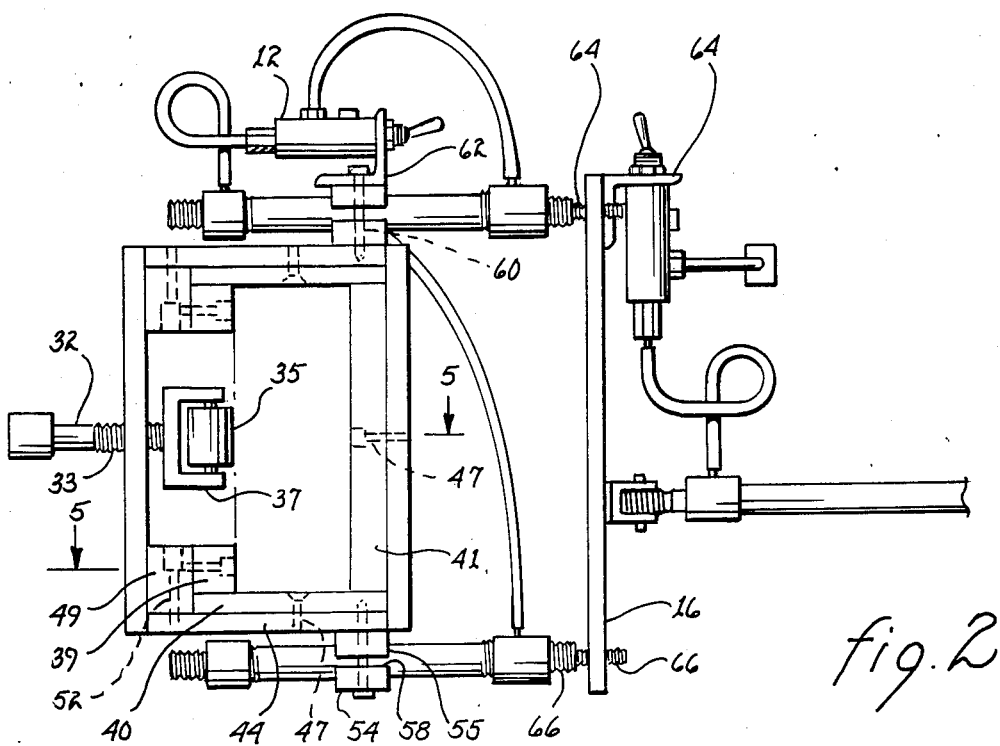

MICROWAVE RADIATING ANTENNAE HYDRAULIC ADJUSTMENT APPARATUS AND METHOD

BACKGROUND OF THE INVENTION

This invention relates generally to a hydraulic adjustment apparatus and method for use in positioning and adjusting microwave radiating antennae or the like. More particularly, the invention relates to at least three hydraulically operated leg members combined to operably join to a base integral to a microwave radiating antennae apparatus. Moreover, the hydraulic adjustment apparatus for the present invention is suitable for moveably mounting onto a support apparatus for more effective use of said microwave radiating antennae.

Conventionally, apparatuses for use in examining or treating various parts of a human body need to be adjustable yet stable. Moreover, when each of said apparatuses is adjusted to a desired position adjacent to said human parts, the desired position must be maintained accordingly locked efficiently to provide a more accurate examination and treatment. Unfortunately, conventional apparatuses provide ball-bearing joints, as well as friction plates which often create problems of being jammed or worn out. Further, a constant upkeep in making sure that proper lubrication is maintained can be a significant disadvantage.

Moreover, conventional adjusting apparatuses for examining or treating patients may have difficulty in providing adjustments in minute increments, especially when relatively small parts of the human body is involved.

Accordingly, there is a dire need for an efficient, economical, simply constructed and easily installed hydraulic adjustment apparatus and method for use in positioning and adjusting microwave radiating antennae or the like, especially for examination or treating certain parts of the body which requires sensitively minute apparatus adjustments and sturdy positioning. Moreover, the adjustment apparatus and method of the present invention should embody a simply constructed combination of inexpensive, easily accessible and rapidly manufactured parts, yet efficient to function with microwave radiating antennae or the like for generally treatment monitoring of patients.

SUMMARY OF THE INVENTION

It is an object of the present invention to provide a hydraulic adjustment apparatus and method for use generally in the treatment monitoring of patients.

It is still another object of the present invention to provide a hydraulic adjustment apparatus and method for use in positioning and adjusting microwave radiating antennae.

It is still another object of the present invention to provide a hydraulic adjustment apparatus and method which may be economically assembled in a compact form having few parts which may be operably coupled to generally patient treatment monitoring apparatus.

It is a further object of the present invention to provide a hydraulic adjustment apparatus and method which may be adjusted in a multi-directional manner, as well as in minute incremental adjustments.

It is a further object of the present invention to provide a hydraulic adjustment apparatus and method which may sturdily lock at a desired position without unnecessary disturbance of a resulting position for said microwave radiating antennae or any other patient treatment monitoring apparatus.

It is yet another object of the present invention to accomplish the above by a hydraulic adjustment apparatus and method utilizing therefrom parts which will be durable in construction, long lasting, economical and efficient when in use.

It is a more particular object of the present invention to provide a hydraulic adjustment apparatus and method for use with apparatus for treatment monitoring of patients incorporating therein a plurality of hydraulically adjusted legs suitable for being operated by a plurality of flexible tubular members for housing therein liquid medium and a plurality of switch valves integrally connected thereto for controlling said liquid medium and thereby for adjusting said plurality of flexible tubular members to subsequently adjust the treatment monitoring apparatus in a multi-directional incremental manner for a final locking position when desired.

It is another more particular object of the present invention to provide a hydraulic adjustment apparatus and method further embodying therein a mounting means suitable for being moveably mounted thereto onto a support apparatus for effective use of said treatment monitoring apparatus.

In accordance with one embodiment of this invention, at least three hydraulically adjusted leg members operably coupled at a common first end of said leg members to a base member for integral connection to microwave radiating antennae, treatment monitoring device, or the like. Moreover, the hydraulic adjustment apparatus of the present invention has at a common second end of said leg members a mounting means generally comprising a box-like member suitable for accommodating therein a support member to allow slidably coupling thereto.

The foregoing and other objects, features and advantages of this invention will be apparent from the following, more particular description of the preferred embodiments of this invention, as illustrated in the accompanying drawings.

BRIEF DESCRIPTION OF THE DRAWINGS

FIG. 1 is a perspective view of a hydraulic adjustment apparatus of the present invention for attaching to a microwave radiating antennae.

FIG. 2 is a side elevational view of the hydraulic adjustment apparatus of the present invention showing an upper portion.

DESCRIPTION OF THE PREFERRED EMBODIMENT

Figure 3:
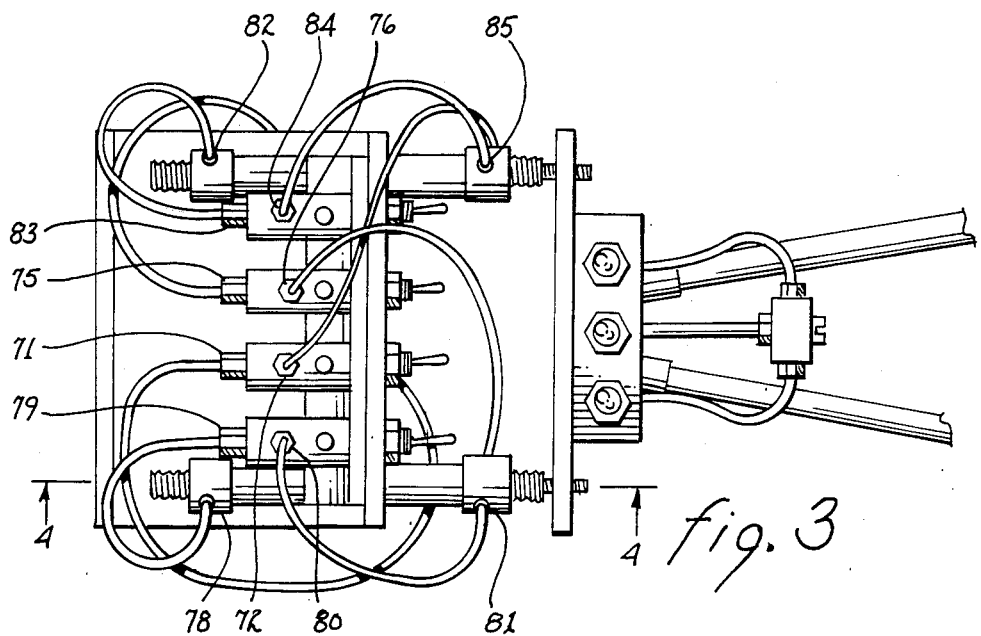
FIG. 3 is a side elevational view of the hydraulic adjustment apparatus of the present invention showing the manner in which the upper portion accommodates therein a plurality of tubular members for housing therein liquid medium.

FIG. 1 is a perspective view of a hydraulic adjustment apparatus generally designated by reference number 1. Here, the hydraulic adjustment apparatus 1 has an upper portion 3, generally embodying therein a box-like member 5 suitable for accommodating therein a mounting member 7; a plurality of upper adjustable leg members 8, 9, 10, 11; a plurality of upper switch valves 12 with associated plurality of upper tubular members 14 attached thereto; as well as a plate member 16 for joining said upper portion 3 to a lower portion 18 of the hydraulic adjustment apparatus 1.

As further shown in FIG. 1, the lower portion 18, generally comprises a plurality of lower switch valves 20 with associated plurality of lower tubular members 22; and lower adjustable legs 24 operably coupled to a base member 26 having a preferable microwave radiating antenna 30 integrally coupled thereto.

As more clearly shown in FIG. 2, the upper portion 3 has passing through thereabove the box-like member 5, an upper threaded member 32 having a threaded portion 33 integral thereto to allow axial adjustment. At the bottom portion of the threaded member 32 is a wheel member 35 operably mounted thereto a brace member 37. The combined threaded member 32 and wheel member 35 would permit slidable mounting of the upper portion 3 of the hydraulic adjustment apparatus 1 onto the mounting member 7. As further shown in FIG. 2, solid lubricant 39, 40, 41 are sturdily connected along the inner surface of the box-like member 5 to permit efficient movement of said upper portion 3 along the mounting member 7 when in operation. Each solid lubricant 40, 41 is coupled to each of side member 44, 45, respectively, by at least one screw member 47 or the like, while each solid lubricant 39 is coupled to an inner member 49 by another screw member 50 or the like. The inner member 49 is preferably coupled to the side member 44 of the upper portion 3 by yet another screw member 52 or the like.

Figure 4:
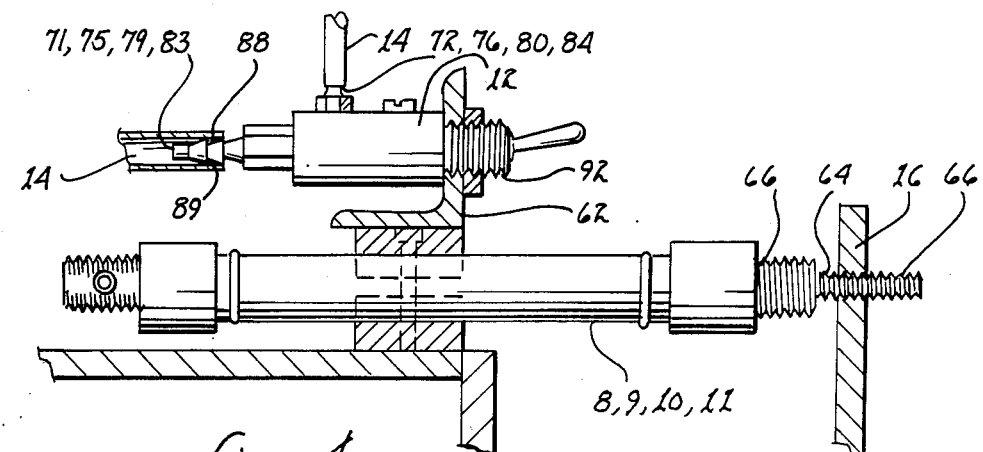
FIG. 4 is a partial cross-sesctional view of an upper adjustable leg member with an associated switch valve taken along line 4—4 of FIG. 3 of the hydraulic adjustment apparatus of the present invention.

As further shown in FIG. 2 (see also FIG. 4, infra.), each of the upper adjustable leg members 8, 9, 10, 11 are coupled to the box-like member 5 by at least a pair of preferably elongated bar members 54, 55 having therebetween a plurality of spaces 58 (as also shown in FIG. 1, supra.) to accommodate therein the plurality of the upper adjustable leg members 8, 9, 10, 11. The pair of preferably bar members 54, 55 are coupled to the side member 44 by a preferably long screw member 60. The plurality of upper switch valves 12 are coupled to the upper portion 3 preferably proximately adjacent the upper adjustable leg members 8, 9 by an elongated L-shaped member 62 (as also shown in FIG. 4, infra.). The lower end 64 of each upper adjustable leg member 8, 9, 10, 11 is coupled to the plate member 16 by thread means 66 (see also FIG. 4, infra.) to allow thereby the desired adjustment of the lower end 64 from the intermediate portion 66 of each of the plurality of upper adjustable leg members 8, 9, 10, 11. The plurality of lower switch valves 20 are attached to the plate member 16 preferable on the same side of the box-like member 5 wherein the plurality of upper switch valves 12 are located. The plurality of lower switch valves 20 are attached to the plate member 16 by another elongated L-shaped member 64 coupled thereto by the preferably long screw member 60 onto one of the outer bar members 54.

In FIG. 3, the plurality of upper tubular members 14 are operably coupled between the upper adjustable leg members 8, 9, 10, 11 and upper switch valves 12 in a manner which would maximize the upper adjustable leg members 8, 9, 10, 11 when in operation, as will later be discussed. Here (see also FIG. 1, supra.), a tubular member 14 connected to a top inlet/outlet member 70 of the upper adjustable leg member 10 attaches to a top inlet/outlet member 71 of one of the upper switch valves 12 and further connects therefrom to a front inlet/outlet member 72 of said upper switch valve 12. Tubular member 14 further connects therebetween said front inlet/outlet member 72 to a bottom inlet/outlet member (not shown) of the upper adjustable leg member 11 a top inlet/outlet member 74 of the upper adjustable leg member 11 joins with a top inlet/outlet member 75 of one of the upper switch valves 12 by a tubular member 14 therebetween. A front inlet/outlet member 76 of said upper switch valve 12 is coupled to said top inlet/outlet member 75 by the tubular member 14 while, also a tuular member 14 is operably coupled therebetween the front inlet/outlet member 76 and a bottom inlet/outlet member 77 of the upper adjustable leg member 10.

Operably joined also by a tubular member 14 is a top inlet/outlet member 78 of the upper adjustable leg member 8 to a top inlet/outlet member 79 of one of the upper switch valves 12 and subsequently joining thereto a front inlet/outlet member 80 of said upper switch valve 12. Said front inlet/outlet member 80 is joined thereto by a tubular member 14 to a bottom inlet/outlet member 81 of the upper adjustable leg member 8 which is thereafter connected thereto a top inlet/outlet member 82 of the upper adjustable leg member 11 by a tubular member 14. Said top inlet/outlet member 82 is operably coupled by a tubular member 14 to a top inlet/outlet member 83 of one of the upper switch valves 12; thereafter connected thereto a front inlet/outlet member 84 of said upper switch valve 12 by a tubular member 14. Said front inlet/outlet member 84 is subsequently joined by a tubular member 14 to a bottom inlet/outlet member 85 of the upper adjustable leg member 9.

Each of the top inlet/outlet members 71, 75, 79, 83 of the plurality of upper switch valves 12 accommodates the tubular member 14 in a snug fitting manner by inserting therein said tubular member 14 a spout member 88, having a series of inclined precipices 89, integral to the top portion of each of the plurality of upper switch valves 12. Similarly, a tubular member 14 is connected thereto each of the front inlet/outlet members 72, 76, 80, 84 in a manner discussed immediately thereabove. At the bottom portion of each of the plurality of the upper switch valves 12 is a toggle switch member 92 integral thereto. Each of the upper 12, as well as the lower 20 switch valves, is conventional similar to that manufactured by Clippard Co. of Cincinnati, Ohio.

Figure 5:
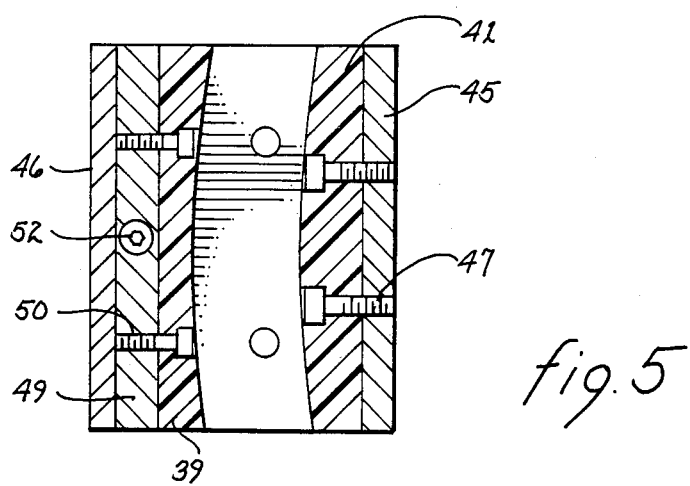
FIG. 5 is a cross-sectional view taken along line 5—5 of FIG. 2 showing the manner in which solid lubricant and metal portions of the upper portion of the hydraulic adjustment apparatus of the present invention are integrally attached.

As previously discussed, shown in FIG. 5 is at least one screw member 47 or the like integrally coupling solid lubricant 41 to side member 45. Similarly, at least another screw member 50 or the like integrally couples solid lubricant 39 to the inner member 49 as well as another side member 46. As further shown in FIG. 5, at least one other screw member 52 or the like integrally couples said inner member 49 to the side member 44 (see FIG. 2, supra.).

Figure 6:
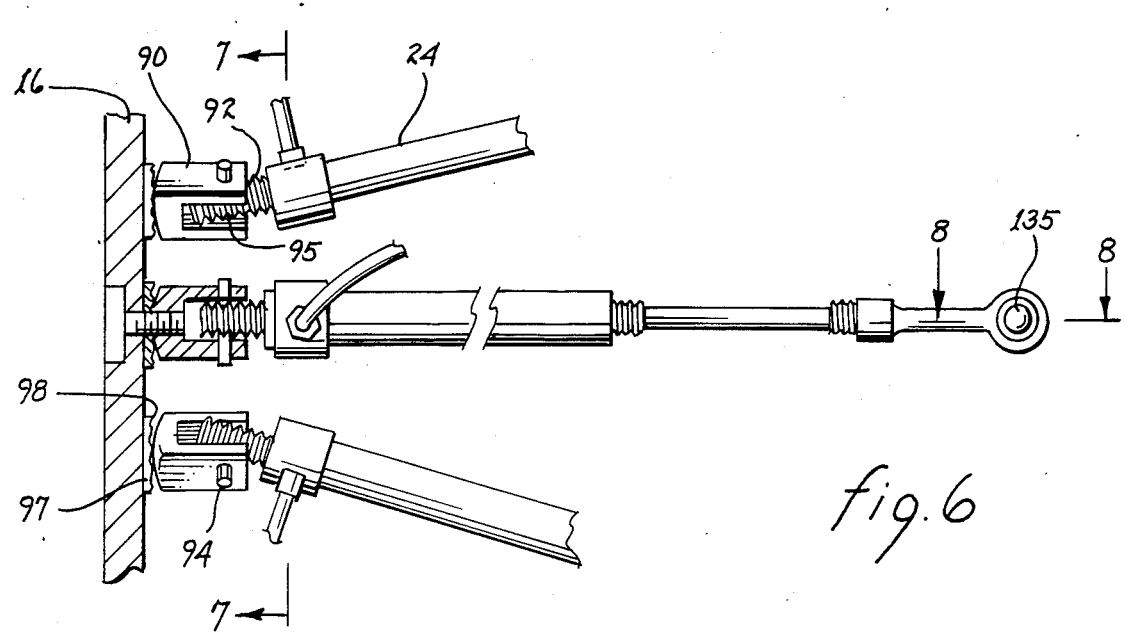
FIG. 6 is a partial cross-sectional view showing the manner in which a plurality of lower adjustable leg members are operably attached to an associated plate member of said upper portion of the hydraulic adjustment apparatus of the present inveniton.

As illustrated in FIG. 6, each of the lower adjustable legs 24 are operably coupled to the plate member 16 by at least one skirt-type member 90 for accommodating therein a threaded portion 92 of the lower adjustable leg 24. An elongated piece member 94 passes therethrough opposing sides of the threaded portion 92 as well as opposing sides of the skirt-type member 90. In order for the lower adjustable legs 24 to laterally adjust, at least a pair of slotted portion 95 passes therethrough opposing sides of said skirt-type member 90, as shown in FIG. 6. Moreover, a preferably metallic washer member 97 abuts the plate member 16 and the skirt-type member 90 therebetween. In order to maximize the snug coupling of said skirt-type member 90 onto the plate member 16, the metallic washer member has a plurality of teeth-like members 98 integral thereto abutting said skirt-type member 90.

Figure 7:
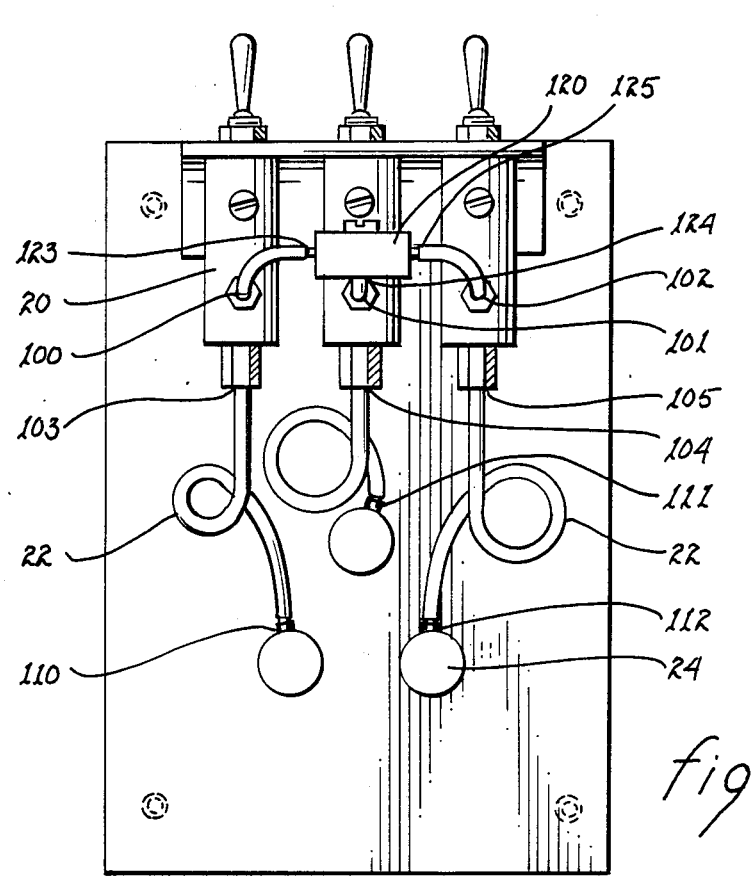
FIG. 7 is a plan view taken along line 7—7 of FIG. 6 showing the manner in which a plurality of lower switch valves are joined underneath said associated plate member relative to said lower adjustable legs of the hydraulic adjustment apparatus of the present invention.
Figure 8:
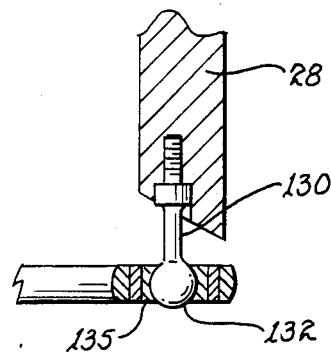
FIG. 8 is a cross-section taken along line 8—8 of FIG. 6 showing how a lower end of each lower adjustable leg is operably attached to a base member integrally joined to the microwave radiating antennae of the hydraulic adjustment apparatus of the present invention.

In FIG. 7, the manner in which the plurality of lower tubular members 22 are coupled to the plurality of lower switch valves 20 is shown; the attachment of which is similar to that previously discussed above for the plurality of tubular members 14 to the plurality of upper switch valves 12 by the use of the spout member 88, as shown in FIG. 4, supra.. A three-way input/output valve member 120 is provided and coupled thereto by a lower tubular member 22 to bottom inlet/outlet members 100, 101, 102 of the lower switch valves 20. A lower tubular member 22 connects thereto a first input/output member 123 of the three-way input/out valve member 120 to the bottom input/output member 100 of a lower switch valve 20; and between a second input/output member 123 of the three-way input/output valve member 120 and the bottom input/output member 101 of a lower switch valve 20; as well as between a third input/output member 125 of the three-way input/output valve member 120 and the bottom input/output member 102 of a lower switch valve 20. Moreover, a lower tubular member 22 operably couples a back input/output member 103 of another lower switch valve 20 to an input/output member 110 of a lower adjustable leg member 24. A back input/output member 103 of another lower switch valve 20 has coupled therebetween an input/output member 111 of another lower adjustable leg member 24 by another lower tubular member 22. Similarly, a lower tubular member 22 operably joins an input/output member 112 of yet another lower adjustable leg member 24 to a back input/output member 105 of yet another switch valve 20.

In order to hydraulically adjust the plurality of upper adjustable leg members 8, 9, 10, 11 as well as the plurality of lower adjustable leg members 24, the plurality of upper 14 and lower 22 tubular members accommodate therein conventional liquid medium suitable for standard use in hydraulically operated devices. When adjustment in the upper 8, 9, 10, 11 and lower 24 adjustable leg members are desired, switch members integral to the upper 12 and lower 20 switch valves positioned in one location and turned towards another location, singly or in combination, when a sturdy position of the upper 8, 9, 10, 11 and lower 24 adjustable leg members, singly or in combination, is desired.

In order to further achieve adjustment when the integrally connected microwave radiating antenna 30 is in use, protruding member 130 originates from the base member 28. Each protruding member 130 preferably has a spherical head member 132 suitable for adjustably and moveably accommodating therein an aperture 135 (see FIG. 6, supra.) passing therethrough the lower end of each of the lower adjustable leg members 24.

Figures 9, 10:
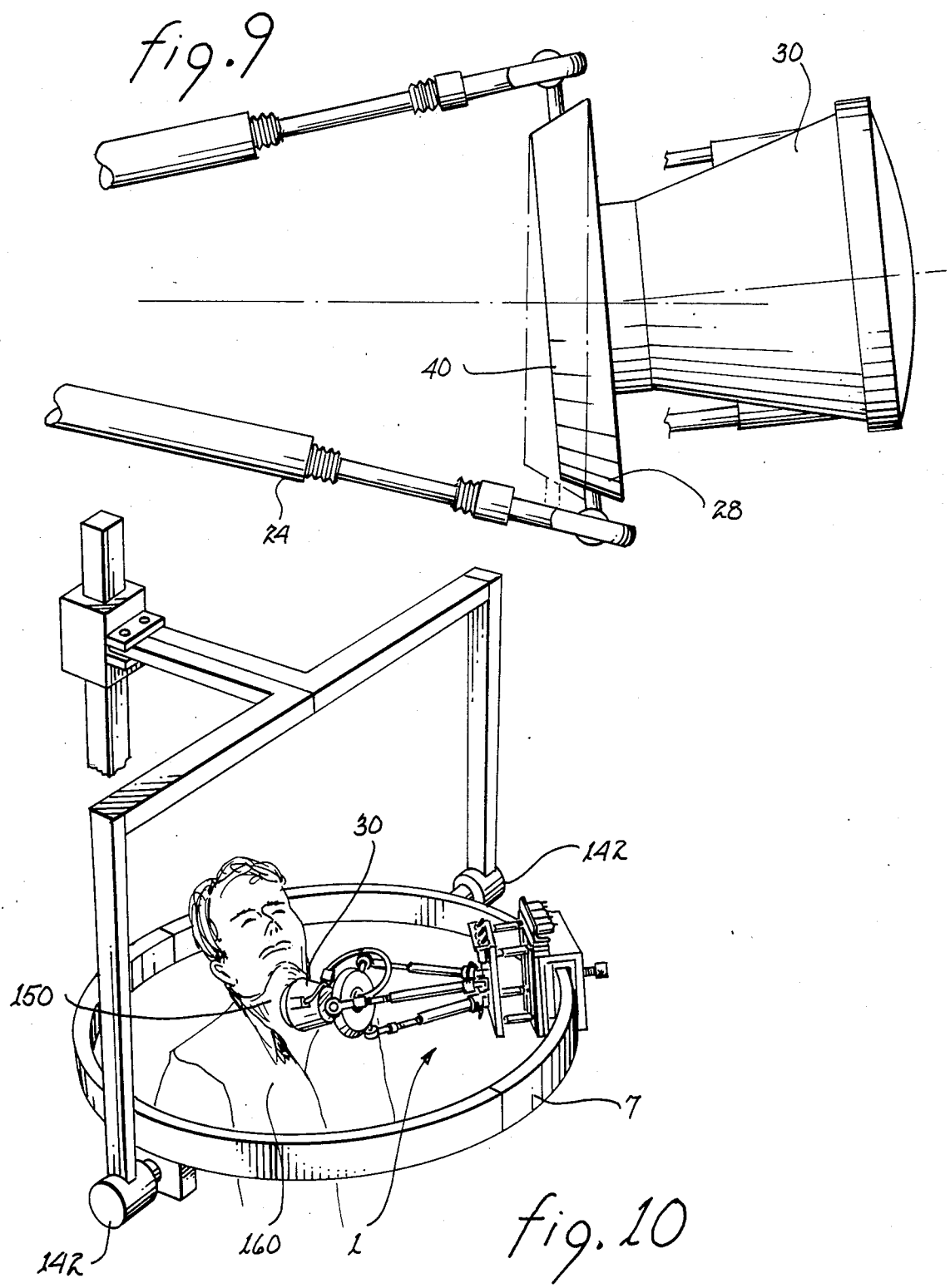
FIG. 9 is a side elevational view of an associated microwave radiating antenna operably joined to the plurality of lower adjustable legs of the hydraulic adjustment apparatus of the present invention.
FIG. 10 is a perspective view of an associated mounting apparatus which may operably accommodate the hydraulic adjustment apparatus of the present invention when in use for effective treatment monitoring of a patient.

As shown in FIG. 9, a conventional microwave radiating antenna 30 is accommodated therein a centrally located aperture 140 (see also FIG. 1, supra.) passing therethrough the base member 28 for adjustably and moveably coupling to the lower adjustable legs 24 thereto.

When in use, as clearly shown in FIG. 10, the hydraulic adjustment apparatus 1 is suitable for slidably mounting onto a mounting member 7, as previously discussed. Said mounting member is preferably circular, as shown, as well as being able to rotate around at least a pair of support members 142 for allowing adjustment of said mounted hydraulic adjustment apparatus, as well as microwave radiating antenna therethroughout a targeted portion 150 in the body of a patient 160, as shown in FIG. 10.

While the invention has been particularly shown and described in reference to preferred embodiments thereof, it will be understood by those skilled in the art that changes in form and details may be made without departing from the spirit and scope of the invention.

I claim:

1. A hydraulic adjustment apparatus for use in adjusting and positioning microwave radiating antenna, comprising:

an upper portion suitable for slidably mounting onto a mounting member means;

a plurality of upper switch valve means integrally coupled to said upper portion for operably manipulating the axial distance between said upper portion from a lower portion of said hydraulic adjustment apparatus;

a plurality of upper adjustable leg member means for operably coupling to said upper switch valve means;

a plurality of lower adjustable leg member means coupled to said plurality of upper adjustable leg member means for adjusting desired positions of said lower portion of said hydraulic adjustment apparatus;

means for mounting one end of each of said plurality of upper adjustable leg member means and one end of each of said plurality of lower leg member means;

support means connected to another portion of each of said plurality of upper and lower leg member means for providing support thereof; and a plurality of lower switch valve means integral to said lower portion for operably coupling to said plurality of lower adjustable leg member means.

2. The hydraulic adjustment apparatus as in claim 1 further comprising a base plate member means adjustably coupled to the lower ends of said plurality of lower adjustable leg member means for integrally coupling thereto a microwave radiating antenna.

3. The hydraulic adjustment apparatus as in claim 2 further comprising a plurality of upper tubular members for coupling said plurality of upper switch valve means to said plurality of upper adjustable leg member means.

4. The hydraulic adjustment apparatus as in claim 3 further comprising a plurality of lower tubular members for operably coupling said plurality of lower switch valve means to said pluraltiy of lower adjustable leg member means.

5. The hydraulic adjustment apparatus as in claim 4 wherein said upper portion suitable for slidably mounting onto a mounting member means has a box-like configured member having at least a pair of opposingly open-ended sides for accommodating therethrough said mounting member means.

6. The hydraulic adjustment apparatus as in claim 5 wherein said upper portion further has integral thereto solid lubricant substantially extending along the inner surfaces of said box-like configured member.

7. The hydraulic adjustment apparatus as in claim 6 wherein said upper portion further has a threaded member means having a wheel member located internal to said box-like configured member, said threaded member means adjustably passes therethrough in an axial direction at least one side of said box-like configured member for operably locking said upper portion of said hydraulic adjustment apparatus onto said mounting member means, said wheel member is suitable for being adjusted so that wheel member rotation locks along said mounting member means.

8. A method for adjusting a patient treatment monitoring device, comprising the steps of:
   integrally coupling a microwave radiating antenna onto a lower portion of a hydraulic adjustment apparatus;
   slidably mounting an upper portion of said hydraulic adjustment apparatus onto a mounting member means;
   locking said upper portion of said hydraulic adjustment apparatus onto said mounting member means;
   manipulating a plurality of upper hydraulically-operated switch valve means integral to said upper portion;
   axially adjusting a plurality of upper hydraulically-operated adjusutable leg member means operably coupled to said plurality of upper hydraulically-operated switch valve means;
   manipulating a plurality of lower hydraulically-operated switch valve means integral to said lower portion;
   adjusting a plurality of lower hydraulically-operated adjustable leg member means operably coupled to said plurality of lower hydraulically-operated switch valve means; and thereafter
   adjusting said microwave radiating antenna operably coupled to the loewr ends of said plurality of lower hydraulically-operated adjustable leg member means on a desired portion of a body of a patient requiring treatment monitoring.

9. The method for adjusting a patient treatment monitoring device as in claim 8 further comprising the step of adjusting said mounting member means having mounted thereon said hydraulic adjustment apparatus for achieving a better desired position in targeting said portion of said body of said patient requiring treatment monitoring.

* * * * *